(12) United States Patent
Woeldicke et al.

(10) Patent No.: US 9,611,466 B2
(45) Date of Patent: Apr. 4, 2017

(54) MODIFIED ENTEROKINASE LIGHT CHAIN

(71) Applicant: Novo Nordisk A/S, Bagsvaerd (DK)

(72) Inventors: Helle Fabricius Woeldicke, Lynge (DK); Xujia Zhang, Beijing (CN); Yun Liu, Beijing (CN); Weiwei Tong, Beijing (CN)

(73) Assignee: Novo Nordisk A/S, Bagsvaerd (DE)

( * ) Notice: Subject to any disclaimer, the term of this patent is extended or adjusted under 35 U.S.C. 154(b) by 0 days.

(21) Appl. No.: 14/364,464

(22) PCT Filed: Dec. 20, 2012

(86) PCT No.: PCT/EP2012/076372
§ 371 (c)(1),
(2) Date: Jun. 11, 2014

(87) PCT Pub. No.: WO2013/092855
PCT Pub. Date: Jun. 27, 2013

(65) Prior Publication Data
US 2015/0064744 A1    Mar. 5, 2015

(30) Foreign Application Priority Data

Dec. 23, 2011  (WO) ................ PCT/CN2011/002169

(51) Int. Cl.
  *C12N 9/64* (2006.01)
  *C12P 21/06* (2006.01)
  *C12N 15/62* (2006.01)

(52) U.S. Cl.
  CPC ............ *C12N 9/6424* (2013.01); *C12P 21/06* (2013.01); *C12Y 304/21009* (2013.01); *C07K 2319/50* (2013.01); *C12N 15/62* (2013.01)

(58) Field of Classification Search
  None
  See application file for complete search history.

(56) References Cited

FOREIGN PATENT DOCUMENTS

| CN | 1470634 A | 1/2004 |
|---|---|---|
| CN | 1869236 A | 11/2006 |
| CN | 100557019 C | 11/2009 |
| CN | 102061302 A | 5/2011 |
| KR | 99008525 | 2/1999 |
| KR | 20030097036 | 12/2003 |
| WO | 2008136014 A1 | 11/2008 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
S Peter et al. Surface Supercharged human enteropeptidase light chain shows improved; solubility and refolding yield, "Protein Engineering Design and Selection", Year 2011, vol. 24, No. 3, pp. 261-268.
Ågren Lena et al. Hydrophobicity engineering of cholera toxin A1 subunit in the strong adjuvant fusion protein CTA1-DD, "Protein Engineering", Year 1999, vol. 12, No. 2, pp. 173-178.
Chun Haarin et al. Design and efficient production of bovine enterokinase light; chain with higher specificity in *E. coli*, "Biotechnol Lett", Year 2011, vol. 33, No. 6, pp. 1227-1232.
Database Geneseq Sep. 1, 2011 (Sep. 1, 2011),; "Targeted soluble protein TrxHis.SEQ; I D : 5 .", XP002693798; retrieved from EBI accession No. GSP:AZJ84253.
Gasparian M E et al. Expression, purification, and characterization of human; enteropeptidase catalytic subunit in *Escherichia coli*, "Protein Expression and Purification" Year 2003, vol. 31, No. 1, pp. 133-139.
Liepnieks J J et al. The Preparation and Properties of Bovine Enterokinase, "Journal Biological Chemistry", Year 1979, vol. 254, No. 5, pp. 1677-1683.
Lu Deshun et al.Crystal Structure of Enteropeptidase Light Chain Complexed with an Analog of the Trypsinogen Activation Peptide, "J. Mol. Biol", Year 1999, vol. 292, No. 2, pp. 361-373.
Su Y et al. The acidity of protein fusion partners predominantly determines; the efficacy to improve the solubility of the target proteins expressed in *Escherichia coli*,; "Journal of Biotechnology", Year 2007, vol. 129, No. 3, pp. 373-382.
Tan Haidong et al. Purification and refolding optimization of recombinant bovine enterokinase light chain overexpressed in *Escherichia coli*, "Protein Expression and Purification", Year 2007, vol. 56, No. 1, pp. 40-47.
Zou Zhoung et al. Hyper-acidic protein fusion partners improve solubility and assist correct folding of recombinant proteins expressed in *Escherichia coli*, "Journal of Biotechnology", Year 2008, vol. 135, No. 4, pp. 333-339.
Kitamoto et al., "Enterokinase, the initiator of intestinal digestion, is a mosaic protease composed of a distinctive assortment of domains," Pro Natl Acad Sci USA, 1994, vol. 91, pp. 7588-7592.
UniProtKB - F7AVP5 (F7AVP5_HORSE), Last modified: Jul. 27, 2011, URL, http://www.uniprot.org/uniprot/F7AVP5, retrieved on Oct. 24, 2016.

* cited by examiner

*Primary Examiner* — Christian Fronda
(74) *Attorney, Agent, or Firm* — Rosemarie R. Wilk-Orescan

(57) ABSTRACT

The present invention is related to novel mammalian enterokinase analogues such as mammalian enterokinase light chain analogues and methods of making such. Also described herein is a method for cleaving proteins having an enterokinase cleavage site.

5 Claims, 12 Drawing Sheets

```
                  1                                                      50
Trx-Linker-EKLM   MSDKIIHLTD DSFDTDVLKA DGAILVDFWA EWCGPCKMIA PILDEIADEY
       Trx-EKLM   MSDKIIHLTD DSFDTDVLKA DGAILVDFWA EWCGPCKMIA PILDEIADEY 51                                                     100
Trx-Linker-EKLM   QGKLTVAKLN IDQNPGTAPK YGIRGIPTLL LFKNGEVAAT KVGALSKGQL
       Trx-EKLM   QGKLTVAKLN IDQNPGTAPK YGIRGIPTLL LFKNGEVAAT KVGALSKGQL 101                                                    150
Trx-Linker-EKLM   KEFLDANLAG SGSGHMHHHH HHSSGLVPRG SGMKETAAAK FERQHMDSPD
       Trx-EKLM   KEFLDANLAG SGSG...... .......... .......... ..........

151                                                    200
Trx-Linker-EKLM   LGTDDDDKIV GGSDSREGAW PWVVALYFDD QQVCGASLVS RDWLVSAAHC
       Trx-EKLM   .GTDDDDKIV GGSDSREGAW PWVVALYFDD QQVCGASLVS RDWLVSAAHC 201                                                    250
Trx-Linker-EKLM   VYGRNMEPSK WKAVLGLHMA SNLTSPQIET RLIDQIVINP HYNKRRKNND
       Trx-EKLM   VYGRNMEPSK WKAVLGLHMA SNLTSPQIET RLIDQIVINP HYNKRRKNND 251                                                    300
Trx-Linker-EKLM   IAMMHLEMKV NYTDYIQPIA LPEENQVFPP GRICSIAGWG AKKYQGSTAD
       Trx-EKLM   IAMMHLEMKV NYTDYIQPIA LPEENQVFPP GRICSIAGWG AKKYQGSTAD 301                                                    350
Trx-Linker-EKLM   VLQEADVPLL SNEKCQQQMP EYNITENMVC AGYEAGGVDS CQGDSGGPLM
       Trx-EKLM   VLQEADVPLL SNEKCQQQMP EYNITENMVC AGYEAGGVDS CQGDSGGPLM 351                                       393
Trx-Linker-EKLM   CQENNRWLLA GVTSFGYQCA LPNRPGVYAR VPRFTEWIQS FLH
       Trx-EKLM   CQENNRWLLA GVTSFGYQCA LPNRPGVYAR VPRFTEWIQS FLH
```

MODIFIED ENTEROKINASE LIGHT CHAIN

CROSS-REFERENCE TO RELATED APPLICATIONS

This application is a 35 U.S.C. §371 National Stage application of International Application PCT/EP2012/076372 (WO 2013/092855), filed Dec. 20, 2012, which claimed priority of International Application PCT/CN2011/002169, filed Dec. 23, 2011

TECHNICAL FIELD

The present invention is related to novel mammalian enterokinase analogues, methods of making such and the use of said mammalian enterokinase analogues for cleaving proteins having an enterokinase cleavage site.

INCORPORATION-BY-REFERENCE OF THE SEQUENCE LISTING

The Sequence Listing, entitled "SEQUENCE LISTING", is 10 kb, was created on 17 Dec. 2012 and is incorporated herein by reference.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jun.e 5, 2014. The Sequence Listing is made up of 10 kilobytes, and the information contained in the attached "SEQUENCE LISTING" is identical to the information in the specification as originally filed. No new matter is added.

BACKGROUND

The serine protease enterokinase (in short enterokinase or EK), also known as enteropeptidase, is a heterodimeric glycoprotein, a mammalian enzyme catalyzing the conversion of trypsinogen into active trypsin. Enterokinase has preference for the substrate sequence Asp-Asp-Asp-Asp-Lys ((Asp)$_4$-Lys, DDDDK), where it selectively cleaves after lysine. Enterokinase isolated from bovine duodenal mucosa exhibits a molecular weight (MW) of 150,000 and a carbohydrate content of 35 percent. The enzyme is comprised of a heavy chain (MW~115,000) and a disulfide-linked light chain (MW~35,000) (Liepnieks et al., J. Biol. Chem., 254 (5): 1677-1683 (1979)). The function of the heavy chain is to anchor the enzyme to the mucosal membrane. The light chain acts as the catalytic subunit.

In E. coli many mammalian proteins are expressed as fusion proteins, which have to be cleaved to release the mature, active protein. For that purpose a processing enzyme is needed, preferably one which cleaves directly at the junction leaving no extra amino acids on the product. Enterokinase is such an enzyme, and much effort has been made to establish a recombinant process to obtain enterokinase or enterokinase analogues in E. coli. However, the results so far have been rather poor: Available commercial products are expensive and of low specific activity, due to inefficient renaturation of precipitated EK or inefficient secretion of soluble EK.

A process in E. coli aiming at a soluble EK product leads to a mixture of soluble and insoluble protein, requiring 2 routes of purification, expensive affinity columns and low yields altogether. In order to get a uniform product, the EK has to be produced as insoluble material in inclusion bodies. They are easy to isolate but challenging to renature in satisfactory yields, due to possible aggregation of the protein.

An object of the invention is to obtain a mammalian enterokinase analogue with improved properties.

SUMMARY

The present invention is related to mammalian enterokinase analogues mutated in appropriate sites. One or more substitutions of an enterokinase analogue of the invention may e.g. be from hydrophobic to hydrophilic, charged amino acids relative to the amino acids in the parent (wild type) mammalian enterokinase.

In one aspect of the invention, a bovine enterokinase light chain analogue is obtained which comprises at least one substitution in position 134 and/or 135 from hydrophobic to a hydrophilic charged amino acid(s). In one aspect, the bovine enterokinase light chain analogue according to the invention further comprises a substitution in position 112.

The invention is also related to a method for obtaining improved solubility in a renaturation process of an enterokinase light chain analogue. In one aspect, the method comprises the step of mutating one or more hydrophobic amino acids of wild type bovine enterokinase light chain to hydrophilic amino acids and optionally mutating other amino acids of wild type bovine enterokinase light chain, wherein the hydrophobic amino acids subject to mutation are present on the surface of folded wild type bovine enterokinase light chain.

In one aspect, the invention provides an improved production process for obtaining mammalian enterokinase analogues. Also or alternatively, in a second aspect, the invention provides an improved production process resulting in improved production yield.

In one aspect of the invention, the method for production of a bovine enterokinase light chain analogue comprises the steps:
  a) culturing the host cells in a growth medium comprising inducer, wherein the host cells comprise a polynucleotide sequence encoding the amino acid sequence of the enterokinase light chain analogue;
  b) recovering the cells with enterokinase light chain analogue in inclusion bodies
  c) solubilizing and refolding the enterokinase light chain analogue; and
  d) purifying the enterokinase light chain analogue.

In one aspect, the invention provides a method for recombinantly producing a peptide or protein in a bacterial or yeast host cell. In one aspect the method comprises:
  a) expressing in yeast or bacteria a fusion protein comprising the peptide or protein to be produced;
  b) cleaving the fusion protein with a bovine enterokinase light chain analogue according to any one of aspects 1-9; and
  c) isolating the produced peptide or protein.

The invention may also solve further problems that will be apparent from the disclosure of the exemplary embodiments.

BRIEF DESCRIPTION OF DRAWINGS

FIG. 10: Comparison of amino acid sequences trxEK$_{LM}$ (SEQ ID No: 9) and trx-linker-$EK_{LM}$ (SEQ ID No: 8). In trx-linker-$EK_{LM}$ the spacer between trx and $EK_{LM}$ is 37 amino acids longer than in trxEK$_{LM}$.

DESCRIPTION

Figure 1:
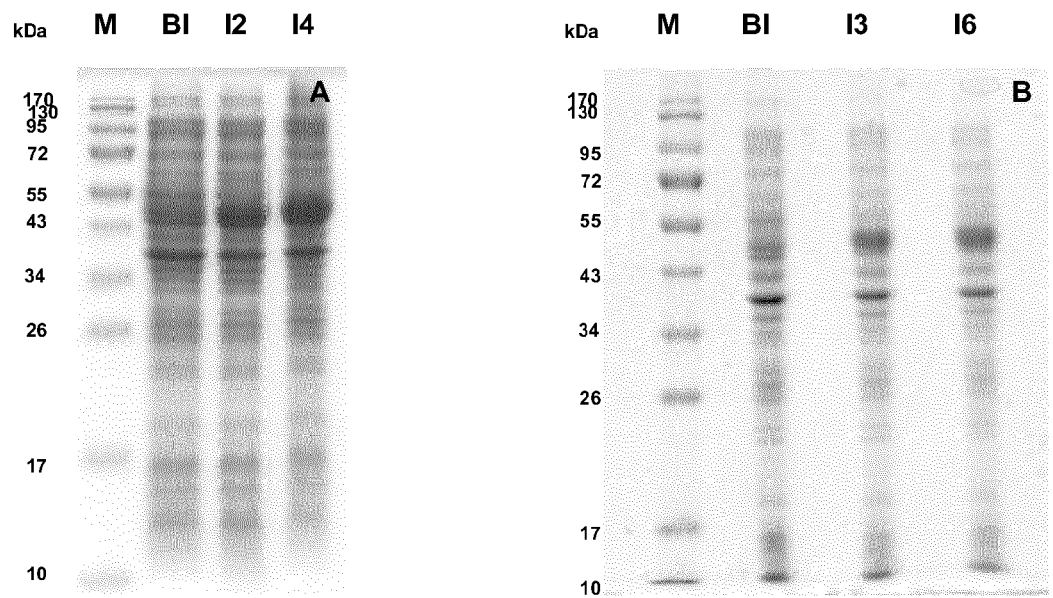
FIG. 1: Dependence of both Trx-EK$_L$ (A) and Trx-EK$_{LM}$ (B) expression upon induction time. M: Marker; BI: Before Induction; I2, I3, I4 and I6 represent induction time (hr) by IPTG, respectively; 15% gel; Fermentation defined medium (FDM) used.

The present invention is related to mammalian enterokinase analogues mutated in appropriate sites. One or more substitutions of an enterokinase analogue of the invention may e.g. be from hydrophobic to hydrophilic, charged amino acids relative to the amino acids in the parent (wild type) mammalian enterokinase. In one aspect, one or more substitutions of a mammalian enterokinase analogue of the invention is from hydrophobic to hydrophilic, charged amino acids relative to the amino acids in wild type bovine enterokinase. In one aspect, the hydrophobic amino acids subject to mutation are present on the surface of folded wild type mammalian enterokinase light chain such as folded wild type bovine enterokinase light chain.

The wild type bovine enterokinase light chain generally exhibits good activity in the presence of various detergents and denaturants over a wide pH range (4.5-9.5) and temperature range (4-45° C.). Therefore, the enterokinase light chain as a powerful tool has been used in biotechnology for the in vitro cleavage of fusion proteins.

However, the complicated production processes and low production yield extracted from animals, such as porcine and bovine, has set a limitation to EK application in biotechnology. Recently, recombinant enterokinase light chain in *E. coli* has been obtained by secretion of active enterokinase light chain or by intracellular accumulation of inclusion bodies of inactive enterokinase light chain, refolding and activation. Moreover, it has been demonstrated that substitution of Cys112 to Ala of bovine enterokinase light chain enhanced the enzymatic activity, presumably due to facilitated refolding. Cys112 links the light chain to the heavy chain in the holoenzyme and is not an essential part of the light chain.

In one aspect of the invention the mammalian enterokinase analogue is a mammalian enterokinase light chain analogue such as a bovine enterokinase light chain analogue. In one aspect of the invention the mammalian enterokinase analogue is a bovine enterokinase light chain analogue. In one aspect according to the invention the bovine light chain analogue comprises substitution(s) in position 134 and/or position 135. In one aspect the bovine enterokinase light chain analogue comprises substitutions in positions 112, 134 and/or 135. In one aspect, the bovine enterokinase light chain analogue comprises at least two substitutions. In one aspect, the bovine enterokinase light chain analogue comprises at least three substitutions. In one aspect the bovine enterokinase light chain analogue comprises substitutions in positions 112, 134 and 135. In one aspect the bovine enterokinase light chain analogue comprises the substitutions C112A, L134K and I135K.

Novel bovine enterokinase light chain analogues of the invention include those having the primary structural conformation (i.e., amino acid sequence) of the light chain of wild type bovine enterokinase. The light chain of wild type bovine enterokinase has the sequence substantially as set forth in SEQ ID NO:1.

```
                                                   SEQ ID NO: 1
  1  IVGGSDSREG  AWPWVVALYF  DDQQVCGASL  VSRDWLVSAA
     HCVYGRNMEP

51  SKWKAVLGLH  MASNLTSPQI  ETRLIDQIVI  NPHYNKRRKN
     NDIAMMHLEM

101  KVNYTDYIQP  ICLPEENQVF  PPGRICSIAG  WGALIYQGST
     ADVLQEADVP

151  LLSNEKCQQQ  MPEYNITENM  VCAGYEAGGV  DSCQGDSGGP
     LMCQENNRWL

201  LAGVTSFGYQ  CALPNRPGVY  ARVPRFTEWI  QSFLH
```

According to an aspect bovine enterokinase light chain analogues of the invention have enterokinase protease activity. Antibodies to such proteases are also available.

The bovine enterokinase light chain analogue described by the present invention, maintains enterokinase wild type protease activity for use as a restriction proteases to specifically cleave fusion proteins.

The term "bovine enterokinase" as used herein means the bovine enterokinase enzyme whose structure and properties are well-known. Mammalian enterokinases are carbohydrate containing heterodimers with a heavy chain of 650-800 amino acids and a catalytic light chain of around 235 amino acids and an overall homology of 75-80% (Liepniecks et al., J. Biol. Chem. 254, 1677 (1979), Matsushima et al., J. Biol. Chem. 269 (31), 19976 (1994), Kitamoto et al., Biochemistry 34, 4562 (1995) for bovine, porcine and human enterokinase, respectively). Further studies of the catalytic light chains are reported in LaVallie et al., J. Biol. Chem. 268 (31), 23311-17 (1993) on the bovine EK and in Matsushima et al., J. Biochem. 125, 947, (1999) on the porcine EK.

The term "bovine enterokinase light chain" as used herein means the light chain of bovine enterokinase having 4 disulphide bridges. The bovine enterokinase light chain is e.g. described in LaVallie et al, above.

When used herein the term "surface" in connection with amino acids present on the surface of folded wild type bovine enterokinase light chain means amino acids identified as present on the surface of the folded wild type bovine enterokinase light chain on a 3D structure as e.g. described in Mod Base P 98072.

"An enterokinase light chain" according to the invention is herein to be understood as bovine enterokinase light chain or an enterokinase light chain from another species such as porcine or human enterokinase light chain.

The term "enterokinase light chain peptide" as used herein means a peptide which is either bovine enterokinase light chain or an analog or a derivative thereof with enterokinase activity.

As used herein, enterokinase activity means the capability of cleaving peptide or protein substrates at a specific site; for protein substrates, this is generally following the sequence $(Asp)_4$-Lys, or a similar sequence such as those described in Light et al., Anal. Biochem. 106: 199(1980); (a cluster of negatively charged amino acids followed by a positively charged amino acid). Typically, such activity is measured by activation of trypsinogen by cleaving the N-terminal propeptide (containing $(Asp)_4$-Lys) with the enterokinase or enterokinase analogue and subsequently assaying the amount of active trypsin generated using tosyl-arginine-methylester (TAME). Alternatively, enterokinase activity can be measured directly by incubating the enzyme with the peptide substrate Gly $(Asp)_4$-Lys-ss-naphthylamide and measuring the increase in fluorescence (excitation at 337 nm, emission at 420 nm) generated by cleavage and release of the ss-NA (ss-naphthylamide) moiety. See, e.g., Grant et al., Biochem. Biophys. Acta. 567:207(1979). Bovine enterokinase is also active on some trypsin substrates like TAME and BAEE (benzyl-arginine-ethyl-ester).

The term "wild type enterokinase light chain" as used herein is intended to mean an enterokinase light chain before any substitutions according to the invention have been applied thereto.

The term "enterokinase light chain analogue" or "bovine enterokinase light chain analogue" as used herein means a modified bovine enterokinase light chain wherein one or more amino acid residues of the enterokinase light chain have been substituted by other amino acid residues and/or wherein one or more amino acid residues have been deleted from the enterokinase light chain and/or wherein one or more amino acid residues have been added and/or inserted to the enterokinase light chain.

In one embodiment an enterokinase light chain analogue comprises less than 10 amino acid modifications (substitutions, deletions, additions (including insertions) and any combination thereof) relative to bovine enterokinase light chain, alternatively less than 9, 8, 7, 6, 5, 4, 3 or 2 modifications relative to bovine enterokinase light chain. In one aspect an enterokinase light chain analogue comprises 5 amino acid modifications, in one aspect 4 amino acid modifications, in one aspect 3 amino acid modifications, in one aspect 2 amino acid modifications and in one aspect 1 amino acid modification relative to bovine enterokinase light chain.

Modifications in the enterokinase molecule light chain are denoted stating the position and the one or three letter code for the amino acid residue substituting the native amino acid residue. Using the one letter codes for amino acids, terms like 134K and 135K designates that the amino acid in position 134 and 135, respectively, is K. Using the three letter codes for amino acids, the corresponding expressions are 134Lys and 135Lys, respectively. Thus, e.g., 112Ala, 134Lys, 135Lys bovine enterokinase light chain is an analogue of bovine enterokinase light chain where the amino acid in position 112 is substituted with alanine, the amino acid in position 134 is substituted with lysine and the amino acid in position 135 is substituted with lysine.

Herein, the term "amino acid residue" is an amino acid from which, formally, a hydroxy group has been removed from a carboxy group and/or from which, formally, a hydrogen atom has been removed from an amino group.

Examples of bovine enterokinase light chain analogues are such wherein Leu in position 134 is substituted with Lys or another charged amino acid, at position 135 where Ile is substituted with Lys or another charged amino acid. Furthermore, Cys in position 112 may be substituted with a number of amino acids including Ala and Ser.

Further examples of bovine enterokinase light chain analogues according to the invention include, without limitation: 134Lys bovine enterokinase light chain; 135Lys bovine enterokinase light chain; 134Lys, 135Lys bovine enterokinase light chain; 112Ala, 134Lys, 135Lys bovine enterokinase light chain; 112Ala, 134Lys bovine enterokinase light chain; 112Ala, 135Lys bovine enterokinase light chain and any such combinations including substitutions with other charged amino acids.

In one aspect a bovine enterokinase light chain analogue is obtained which has improved solubility in a renaturation process relative to natural bovine enterokinase light chain. In one aspect a bovine enterokinase light chain analogue according to the invention has one or more surface oriented hydrophobic amino acids which have been mutated to hydrophilic, charged amino acids wherein improved solubility in a renaturation process relative to natural bovine enterokinase light chain is obtained. In one aspect surface oriented hydrophobic amino acids for substitution to hydrophilic charged amino acids are selected after aligning the bovine enterokinase light chain with other serine proteases and scanning the solvent-accessable surfaces through a computational 3D model of enterokinase.

The method for refolding a bovine enterokinase light chain analogue according to the invention is known to the person skilled in the art. For example, refolding may be carried out by denaturation in urea, followed by oxidative refolding in glutathione or another re-dox environment.

In one aspect a buffer (refolding buffer) is used during the refolding process. In one aspect of the invention, the refolding buffer comprises urea. In one aspect, the refolding buffer comprises between 0 M and 2 M urea. In one aspect, the refolding buffer comprises between 0.5 M and 2 M urea, between 0 M and 1.5 M urea or between 0.5 M and 1.5 M urea. In one aspect, the refolding buffer comprises about 1 M urea.

The initial concentration of inclusion body may affect the refolding yield. In one aspect of the invention, the concentration of inclusion body is between 1 and 4 mg/ml.

In one aspect of the invention, the thioredoxin (Trx) tag is removed during refolding, i.e. during dilution and incubation under refolding conditions. It has thus been found that refolding and activation may be obtained without addition of an activation enzyme. In one aspect of the invention, the linker connecting the trx tag and the bovine enterokinase light chain analogue of the invention is removed by autocleavage. It has thus by the inventors surprisingly been found that the linker connecting the trx tag and the bovine enterokinase light chain analogue of the invention facilitates the refolding.

In one aspect, less aggregation during the renaturation process of a bovine enterokinase light chain analogue according to the invention is obtained relative to the aggregation obtained during the renaturation process of wild type EK. In one aspect, a bovine enterokinase light chain analogue according to the invention has the substitutions L134K and I135K, where the bovine enterokinase light chain analogue is more soluble during the renaturation process relative to wild type EK. In one aspect, a bovine enterokinase light chain analogue according to the invention further has the substitution C112A. It is believed by the inventors that by mutating the lone cysteine in position 112, which in wild type EK heterodimer is involved in the disulfide binding from the light chain to the heavy chain, formation of the 4 disulfide bridges in the EK light chain may be facilitated.

In one aspect, a bovine enterokinase light chain analogue of the invention has full enterokinase activity compared to wild type bovine enterokinase. In one aspect, a bovine enterokinase light chain analogue of the invention has a substantially equivalent functional or biological activity as wild type bovine enterokinase. For example, a bovine enterokinase light chain analogue has substantially equivalent functional or biological activities (i.e., is a functional equivalent) of the polypeptide having the amino acid sequence set forth as SEQ ID NO: 1 (e.g., has a substantially equivalent enteropeptidase activities).

Nucleic acid forms encoding enterokinase light chain analogues of the present invention are also within the scope of the invention. Nucleic acids according to the invention include genomic DNA (gDNA), complementary DNA (cDNA), synthetic DNA prepared by chemical synthesis as well as DNA with deletions or substitutions, allelic variants and sequences that hybridize thereto under stringent conditions as long as they encode enterokinase light chain analogues of the present invention.

In one embodiment a nucleic acid is provided wherein said nucleic acid comprises a polynucleotide sequence, and wherein said nucleic acid encodes a mammalian enterokinase light chain analogue such as a bovine enterokinase light chain analogue according to the invention. In one embodiment, the nucleic acid is operably linked to an inducible promoter. In one embodiment, a recombinant vector is provided which comprises the nucleic acid operably linked to the inducible promoter. In one embodiment, the inducible promoter is selected from a group consisting of AraB, T7, trp, lac, tac.

A further embodiment of the invention provides a host cell comprising the recombinant vector comprising the polynucleotide sequence coding for the amino acid sequence of a mammalian enterokinase light chain analogue such as a bovine enterokinase light chain analogue according to the invention.

A further aspect of the invention provides the host cell comprising the recombinant vector comprising the polynucleotide sequence coding for the amino acid sequence encoding a mammalian enterokinase light chain analogue such as a bovine enterokinase light chain analogue according to the invention. In one embodiment, the host cell is selected from a group consisting of *E. coli, B. subtilis, S. saccaromyces* and *A. oryzae*.

The production of polypeptides, e.g., enterokinase light chain, is well known in the art. The bovine enterokinase light chain analogue may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999. The bovine enterokinase light chain analogue may also be produced by a method which comprises culturing a host cell containing a DNA sequence encoding the analogue and capable of expressing the bovine enterokinase light chain analogue in a suitable nutrient medium under conditions permitting the expression of the bovine enterokinase light chain analogue. Several recombinant methods may be used in the production of bovine enterokinase light chain and bovine enterokinase light chain analogues. Examples of methods which may be used in the production of enterokinase in microorganisms such as, e.g., *Escherichia coli* and *Saccharomyces cerevisiae* are, e.g., disclosed in WO 94/16083.

Typically, the bovine enterokinase light chain analogue is produced by expressing a DNA sequence encoding the bovine enterokinase light chain analogue in question or a precursor thereof in a suitable host cell by well known technique as disclosed in e.g. WO 94/16083

The bovine enterokinase light chain analogues of the invention may be recovered from the cell culture medium or from the cells. The bovine enterokinase light chain analogues of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J. C. Janson and Lars Ryden, editors, VCH Publishers, New York, 1989).

In one aspect, the bovine enterokinase light chain analogues of the present invention are purified using anion exchange chromatography. In a further aspect, the anion exchange chromatography is followed by hydrophobic interaction chromatography. In one aspect, the bovine enterokinase light chain analogues of the present invention are purified using Q HP anion exchange chromatography. In a further aspect, the Q HP anion exchange chromatography is followed by Phenyl FF hydrophobic interaction chromatography.

In one aspect of the present invention an improved process for production of a mammalian enterokinase light chain analogue such as a bovine enterokinase light chain analogue is provided, wherein said method comprises the steps:
 a) culturing the host cells in a growth medium comprising inducer, wherein the host cells comprise a polynucleotide sequence encoding the amino acid sequence of the enterokinase light chain analogue;
 b) recovering the cells with enterokinase light chain analogue in inclusion bodies
 c) solubilizing and refolding the enterokinase light chain analogue; and
 d) purifying the enterokinase light chain analogue.

The invention provides a new recombinant process for production of mammalian enterokinase light chain analogue such as a bovine enterokinase light chain analogue in *E. coli* in a very efficient and economic way.

The expression of a bovine enterokinase light chain analogue according to the invention may e.g. be localized in the inclusion bodies of *E. coli* or in the secreted material of yeast. In one embodiment expression of enterokinase is localized in the inclusion bodies of *E. coli*.

Various strains of *E. coli* are useful as host cells for the production of non-glycosylated, homogeneous enterokinase activity are also well-known in the art. A non-exclusive list of such strains includes *E. coli* B BL21 DE3, *E. coli* K12 W3110, MC1061, DH1, K803, HB101, JM101 and other K12 like strains. Alternatively, other bacterial species may be used, including *B. subtilis*, various strains of *Pseudomonas*, other bacilli and the like.

Many strains of yeast cells, known to those skilled in the art, are also available as host cells for expression of the enterokinase activity of the present invention. Yeast cells are especially useful as a host for pre/pro fusion to mature enterokinase. When expressed using a suitable yeast vector, the fusion is secreted by virtue of a signal peptide.

When the bovine enterokinase light chain analogue of this invention is expressed in bacterial cells, it may be expressed intracellularly usually as inclusion bodies, or it may be secreted from bacterial cells in active form if a secretory signal is included. Where necessary or desired, as when reduced bioactivity is observed, the enterokinase activity may be obtained by conventional methods such as solubilization of protein in urea or guanidine HCl, followed by dilution to reduce the concentration of these reagents and treatment with oxidizing agents such as dithiothreitol or ss-mercapto ethanol to enhance refolding.

In one embodiment, the bovine enterokinase light chain analogues according to the invention are enzymatically active proteases which cleave specifically after a $(Asp)_4$-Lys (DDDDK) sequence in various numbers of fused protein products between affinity tag and the mature protein. In one embodiment, the bovine enterokinase light chain analogues according to the invention have retained enzymatic activity In one aspect of the invention, a process for preparing a bovine enterokinase light chain analogue in *E. coli* cells is obtained, wherein the *E. coli* cells are transformed with a plasmid carrying the bovine enterokinase light chain analogue gene and an inducible promoter by fermentation involving batch and fed batch stages and isolation and purification of the expressed protein from the cultures.

In one aspect of the invention, a refolding process for a bovine enterokinase light chain analogue according to the invention is obtained, wherein the expression of the enterokinase light chain analogue is in the form of inclusion bodies in recombinant *E. coli*. In one embodiment denaturation followed by refolding in a redox system is used.

The enterokinase light chain analogues of the invention may be used in a method for cleaving proteins having an enterokinase cleavage site, and especially fusion proteins having such a cleavage site engineered into their sequence. The amounts needed are readily determined empirically by one skilled in the art.

The term "fusion protein" as used herein is meant to refer to a protein created through genetic engineering from two or more proteins or peptides. As used herein, a fusion protein can refer to a protein in which a Asp-Asp-Asp-Asp-Lys (D4K) sequence has been intentionally introduced for specific cleavage. Generally, cleavage of the fusion protein generates two polypeptides. A fusion protein according to the invention can be a recombinant fusion protein. In particular embodiments, a fusion protein can be generated, for example, from the addition of a vector-derived residue peptide at one terminus, for example the N-terminus, in addition to the amino acid sequence of the wild type protein of interest. In this way, for example, a recombinant fusion protein can be constructed to have Asp-Asp-Asp-Lys (D4K) cleavage site in the vector upstream joined to the protein of interest.

The term "operably linked" denotes herein a configuration in which a control sequence is placed at an appropriate position relative to the coding sequence of the polynucleotide sequence such that the control sequence directs the expression of the coding sequence of a polypeptide.

The term "protease" is intended to include any polypeptide/s, alone or in combination with other polypeptides, that break peptide bonds between amino acids of proteins.

The term "proteolytic activity" is meant to refer to the cleavage activity of a substrate by an enzyme. In particular embodiments, the term refers to the enzymatic cleavage by enteropeptidases. In exemplary embodiments, the term is meant to refer to the specific activity of a bovine enterokinase light chain analogue of the invention for Asp-Asp-Asp-Asp-Lys cleavage sites. "Non-specific proteolytic activity" is meant to refer to cleavage activity that is not directed to a specific cleavage site. "Specific proteolytic activity" is meant to refer to cleavage activity that is directed to a specific cleavage site.

Indeed, as described herein, a bovine enterokinase light chain analogue according to the invention is superior for cleavage of fusion proteins when compared to the bovine-derived two-chain form.

As another aspect of the invention, the enterokinase light chain analogue of the invention is incorporated as one of the fusion protein partners to yet another protein. As such, with the addition of a minimal amount of exogenous enterokinase activity to the reaction vessel the fusion protein results in the release of additional enterokinase activity which in turn can catalyze many more proteolytic cleavages of fusion proteins. In this way, large amounts of enterokinase activity can be produced from a fusion protein in an autocatalytic manner.

Another particular aspect of the invention teaches a method for cleavage of a protein containing an Asp-Asp-Asp-Asp-Lys cleavage site using any of the bovine enterokinase light chain analogues of the invention described herein, the method comprising contacting the protein with any of the bovine enterokinase light chain analogues of the invention, and wherein the contacting of the protein with the bovine enterokinase light chain analogue results in specific cleavage.

In one embodiment, the protein is a fusion protein. In another embodiment, the fusion protein is a recombinant fusion protein. In a further embodiment, the protein is bacterially produced. In a more particular embodiment, the protein is a synthetic protein.

In a further aspect, the invention teaches a method for the preparation of recombinant protein using any of the bovine enterokinase light chain analogues according to the invention as described herein, the method comprising providing a recombinant fusion protein containing a Asp-Asp-Asp-Asp-Lys cleavage site, and contacting the fusion protein with any of the bovine enterokinase light chain analogues of the invention, wherein contacting the recombinant fusion protein with the bovine enterokinase light chain analogue results in Asp-Asp-Asp-Asp-Lys specific cleavage and preparation of recombinant protein.

The Following is a Non-Limiting List of Aspects According to the Invention:

1. A bovine enterokinase light chain analogue comprising at least one substitution in position 134 and/or 135 from hydrophobic to a hydrophilic charged amino acid(s).
2. The bovine enterokinase light chain analogue according to aspect 1, wherein both positions 134 and 135 have substitutions from a hydrophobic to a hydrophilic charged amino acid.
3. The bovine enterokinase light chain analogue according to aspect 1 or 2, further comprising a substitution in position 112.
4. The bovine enterokinase light chain analogue according to aspect 3, wherein the amino acid in position 112 is selected from the group consisting of: alanine, serine and glycine.
5. The bovine enterokinase light chain analogue according to aspect 3, wherein the amino acid in position 112 is alanine.
6. The bovine enterokinase light chain analogue according to any one of the previous aspects, wherein the hydrophilic charged amino acid(s) are one or more amino acids selected from the group consisting of: lysine, arginine, glutamic acid and aspartic acid.
7. The bovine enterokinase light chain analogue according to any one of the previous aspects, wherein the hydrophilic charged amino acid(s) are lysine.
8. The bovine enterokinase light chain analogue according to any one of the previous aspects, comprising the substitutions C112A, L134K and I135K.
9. The bovine enterokinase light chain analogue according to any one of the previous aspects, wherein the enterokinase light chain to be mutated is SEQ ID NO:1.
10. A method for obtaining improved solubility in a renaturation process of an enterokinase light chain analogue comprising the step of mutating one or more hydrophobic amino acids of wild type bovine enterokinase light chain to hydrophilic amino acids and optionally mutating other amino acids of wild type bovine enterokinase light chain, wherein the hydrophobic amino acids subject to mutation are present on the surface of folded wild type bovine enterokinase light chain.
11. A method according to aspect 10, wherein the hydrophobic amino acid(s) to be mutated are selected from the group consisting of: I, V, L, M, W, F, A
12. A method according to aspect 10, wherein the hydrophobic amino acid(s) to be mutated are selected from the group consisting of: Leucin and isoleucin.
13. A method according to any one of aspects 10-12, wherein the hydrophilic amino acid(s) are selected from the group consisting of: Lysine, arginine, glutamic acid and aspartic acid.
14. A method according to aspect 13, wherein the hydrophilic amino acid(s) are lysine.
15. A method according to any one of aspects 10-14, wherein the hydrophobic amino acid(s) to be mutated are in one or more positions selected from the group consisting of: position 11-14 (amino acids AWPW), position 78-80 (amino acids I V I) and position 133-136 (amino acids A L I Y).
16. A method according to aspect 15, wherein the hydrophobic amino acid(s) to be mutated are in positions 134 and/or 135.
17. A method for production of a bovine enterokinase light chain analogue, wherein said method comprises the steps:
    a) culturing the host cells in a growth medium comprising inducer, wherein the host cells comprise a polynucleotide sequence encoding the amino acid sequence of the enterokinase light chain analogue;
    b) recovering the cells with enterokinase light chain analogue in inclusion bodies
    c) solubilizing and refolding the enterokinase light chain analogue; and
    d) purifying the enterokinase light chain analogue.
18. A method for production of a bovine enterokinase light chain analogue according to aspect 17, wherein a refolding buffer is used during the refolding process.
19. A method for production of a bovine enterokinase light chain analogue according to aspect 17 or 18, wherein the refolding buffer comprises urea.
20. A method for production of a bovine enterokinase light chain analogue according to any one of aspects 17-19, wherein the refolding buffer comprises about 1 M urea.
21. A method for production of a bovine enterokinase light chain analogue according to any one of aspects 19-20, wherein the refolding buffer further comprises low molecular weight polyethylene glycol (low-PEG).
22. A method for production of a bovine enterokinase light chain analogue according to any one of aspects 19-21, wherein the refolding buffer further comprises PEG1000 such as 1% PEG1000.
23. A method for production of a bovine enterokinase light chain analogue according to any one of aspects 19-22, wherein the refolding buffer further comprises hydroxypropyl-β-cyclodextrin such as 1.5% hydroxypropyl-β-cyclodextrin.
24. A method for production of a bovine enterokinase light chain analogue according to any one of aspects 17-23, wherein the concentration of inclusion body is between 1 and 4 mg/ml.

25. A method for production of a bovine enterokinase light chain analogue according to any one of aspects 17-24, wherein the host cell is *E. coli*.
26. A method for production of a bovine enterokinase light chain analogue according to any one of aspects 17-25, wherein the bovine enterokinase light chain analogue is an analogue according to any one of aspects 1-9.
27. A method for recombinantly producing a peptide or protein in a bacterial or yeast host cell, comprising
    a) expressing in yeast or bacteria a fusion protein comprising the peptide or protein to be produced;
    b) cleaving the fusion protein with a bovine enterokinase light chain analogue according to any one of aspects 1-9; and
    c) isolating the produced peptide or protein.
28. A method for recombinantly producing a peptide or protein according to aspect 27, wherein the fusion protein expressed in step a) further comprises an Asp-Asp-Asp-Asp-Lys cleavage site.
29. A method for recombinantly producing a peptide or protein according to aspect 28, wherein step b) results in Asp-Asp-Asp-Asp-Lys specific cleavage.
30. A method for recombinantly producing a peptide or protein according to any one of aspects 27-29, wherein the host cell is *E. coli*.
31. A method for recombinantly producing a peptide or protein according to any one of aspects 27-30, wherein the peptide or protein to be produced is a GLP-1 peptide.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

Herein a production process for making bovine enterokinase light chain analogues has been developed. The bovine enterokinase light chain analogues were fused to thioredoxin tag expressed as inclusion bodies in *E. coli*. After refolding and auto-activation, the active enterokinase light chain analogue was purified by Q HP anion exchange chromatography. Moreover, it was found that triple substitutions (C112A, L134K and I135K) of bovine enterokinase light chain ($EK_{LM}$), which improved the surface hydrophilic properties, increased the refolding yield 4 fold without loosing activity. The yield of purified enterokinase light chain analogue was 800 mg/L from a culture of 4 g/L, and the specific activity was determined as 5000±10 EU/mg. Thus, our enterokinase light chain analogue production process provides a valuable tool for processing therapeutic fusion proteins and other fusion proteins.

ABBREVIATIONS

EK: Enterokinase
$EK_L$: Bovine Enterokinase light chain with C112A mutation
$EK_{LM}$ (alternatively herein named $EK_M$ or $EK_{LM}$(C112A, L134K, I135K)): Bovine Enterokinase light chain with mutations in positions 112 to Ala, 134 to Lys and 135 to Lys.
Trx$EK_{LM}$: $EK_{LM}$ fused with N-terminal Thioredoxin tag with a linker of 12AA
Trx-Linker-$EK_{LM}$: $EK_{LM}$ fused with N-terminal Thioredoxin tag with a longer linker of 49AA
Trx-Linker-$EK_L$: $EK_L$ fused with N-terminal Thioredoxin tag with a longer linker of 49AA
IPTG: Isopropyl β-D-1-thiogalactopyranoside
Tris: Tris(hydroxymethyl)aminomethane
DTT: Dithiothreitol
GSSG: Glutathione disulfide
GSH: Glutathione
FDM: Fermentation defined medium
Trx: Thioredoxin
LC-MS: Liquid chromatography-mass spectrometry
SDS-PAGE: Sodium dodecyl sulfate polyacrylamide gel electrophoresis
BL21: *E. coli* strain *E. coli* B BL21 DE3
PCR reaction: Polymerase chain reaction
Low-PEG: Low molecular weight polyethylene glycol such as polyethylene glycols with a molecular weight up to 1000
PEG1000: Polyethylene Glycol 1000, a polyethylene glycol with approximate molecular weight 1000.

Example 1

Plasmid Construction of Trx-Linker-$EK_E$ and Trx-Linker-$EK_{LM}$

The DNA sequence encoding the catalytic subunit of bovine enterokinase was amplified with the following primers:

```
                                          SEQ ID NO: 2
5'-ggcggtaccgacgacgacgacaagattgtcggagga
agtgac-3'

SEQ ID NO: 3
5'-ggcgaattcctaatgtagaaaactttgtatccactc
tgtgaacc-3'
```

These two primers contained Kpn I and EcoR I restriction enzyme sites, respectively. The target fragment was introduced into pET32a (Novagen) from KpnI and EcoRI site. Routine PCR reaction was performed using Pfu DNA Polymerase from Stratagene. The sequence of plasmid pET32a-$EK_L$ was confirmed by sequencing. Three substitution sites, i.e. C112A, L134K, I135K were introduced by using QuikChange® XL Site-Directed Mutagenesis Kit from Stratagene with the primers:

```
                                                       SEQ ID NO: 4
C112AF 5'-acacagattatatacagcctat tgcgttaccagaagaaaatcaag-3'

SEQ ID NO: 5
C112AR 5'-cttgattttcttctggtaacgcaataggctgtatataatctgtgt-3'

SEQ ID NO: 6
L134K,I135 KF 5'-ctattgctggctgggggcaaagaaatatcaaggttctactgcagacg-3'

SEQ ID NO: 7
L134K,1135KR 5'-cgtctgcagtagaaccttgatatttctttcccc ccagccagcaatag-3'
```

Amino acid Sequence of Trx-linker-EK$_{Lm}$:
                                                       SEQ ID NO: 8
<u>MSDKIIHLTDDSFDTDVLKADGAILVDFWAEWCGPCKMIAPILDEIADEYQGKLTVAKLNIDQ</u>
<u>NPGTAPKYGIRGIPTLLLFKNGEVAATKVGALSKGQLKEFLDANL</u>AGSGSGHMHHHHHSS
GLVPRGSGMKETAAAKFERQHMDSPDLGTDDDDK*IVGGSDSREGAWPWVVALYFDDQQ*
*VCGASLVSRDWLVSAAHCVYGRNMEPSKWKAVLGLHMASNLTSPQIETRLIDQIVINPHY*
*NKRRKNNDIAMMHLEMKVNYTDYIQPI<u>A</u>LPEENQVFPPGRICSIAGWGA<u>KK</u>YQGSTADVLQ*
*EADVPLLSNEKCQQQMPEYNITENMVCAGYEAGGVDSCQGDSGGPLMCQENNRWLLAG*
*VTSFGYQCALPNRPGVYARVPRFTEWIQSFLH*
Underlined: Trx; Regular: linker; **Bold italic: *EK$_{LM}$***

Amino acid Sequence of Trx-EK$_{Lm}$:
                                                       SEQ ID NO: 9
<u>MSDKIIHLTDDSFDTDVLKADGAILVDFWAEWCGPCKMIAPILDEIADEYQGKLTVAKLNIDQ</u>
<u>NPGTAPKYGIRGIPTLLLFKNGEVAATKVGALSKGQLKEFLDANL</u>AGSGSGGTDDDDK*IVGG*
*SDSREGAWPWVVALYFDDQQVCGASLVSRDWLVSAAHCVYGRNMEPSKWKAVLGLHM*
*ASNLTSPQIETRLIDQIVINPHYNKRRKNNDIAMMHLEMKVNYTDYIQPI<u>A</u>LPEENQVFPPGR*
*ICSIAGWGA<u>KK</u>YQGSTADVLQEADVPLLSNEKCQQQMPEYNITENMVCAGYEAGGVDSC*
*QGDSGGPLMCQENNRWLLAGVTSFGYQCALPNRPGVYARVPRFTEWIQSFLH*
Underlined: Trx; Regular: linker; **Bold italic: *EK$_{LM}$***

Example 2

Fermentation and Expression of Trx-Linker-EK$_L$ and Trx-Linker-EK$_{LM}$

Cells from a glycerol stock were inoculated on an EC1 plate grown overnight at 37° C., and washed with 0.9% sodium chloride (NaCl) to suspend the cells. The culture was allowed to grow in a fermentor containing fermentation defined medium (FDM) at 37° C. for 16 hrs, and induced with 1.0 mM IPTG at an OD600 of 150 , and then grown for 6 hours at 37° C. before harvesting by centrifugation.

Both Trx-linker-EK$_L$ and Trx-linker-EK$_{LM}$ in *E. coli* BL21 were expressed in fed-batch fermentation. As shown in FIG. 1, no apparent leaky expression judged by SDS-PAGE was observed before IPTG induction. An induced band just above 43 kD on SDS-PAGE by IPTG appeared, and it was confirmed by LC-MS that this band represented the target protein. Moreover, the expression level of the target protein was dependent upon the induction time. 4 hrs or 6 hrs of induction for Trx-linker-EK$_L$ and Trx-linker-EK$_{LM}$ by using fermentation defined medium (FDM), respectively gave acceptable expression, and ~4 g/L of the target proteins was achieved.

Example 3

Refolding, Auto-Catalytic Activation and Purification

Cells from fermentation were resuspended in lysis buffer (1:10, w/w) containing 20 mM Tris, pH 8.0, and lysed by French press. Inclusion bodies were sedimented at 20,000 g for 1 hr at 4° C., and then washed once by using lysis buffer. The inclusion bodies were solublized to 3.2 mg/ml in buffer containing 20 mM Tris, 8 M urea, pH8.0, 20 mM DTT and incubated at 4° C. for 3 hrs. After centrifugation at 20,000 g for 30 min, the solublized EK (i.e. Trx-linker-EK$_L$ and/or Trx-linker-EK$_{LM}$) was diluted 80 fold into refolding buffer containing 20 mM Tris, 1 M Urea, 1 mM GSSG, 3 mM GSH, pH 8.3 and incubated at 20° C. for 24 hrs.

During dilution and incubation of the refolding procedure, auto-catalytic cleavage occurred, and liberated fully active enzyme without thioredoxin (Trx) tag. Finally, the enzyme was purified by Q HP anion exchange chromatography.

Figure 2:
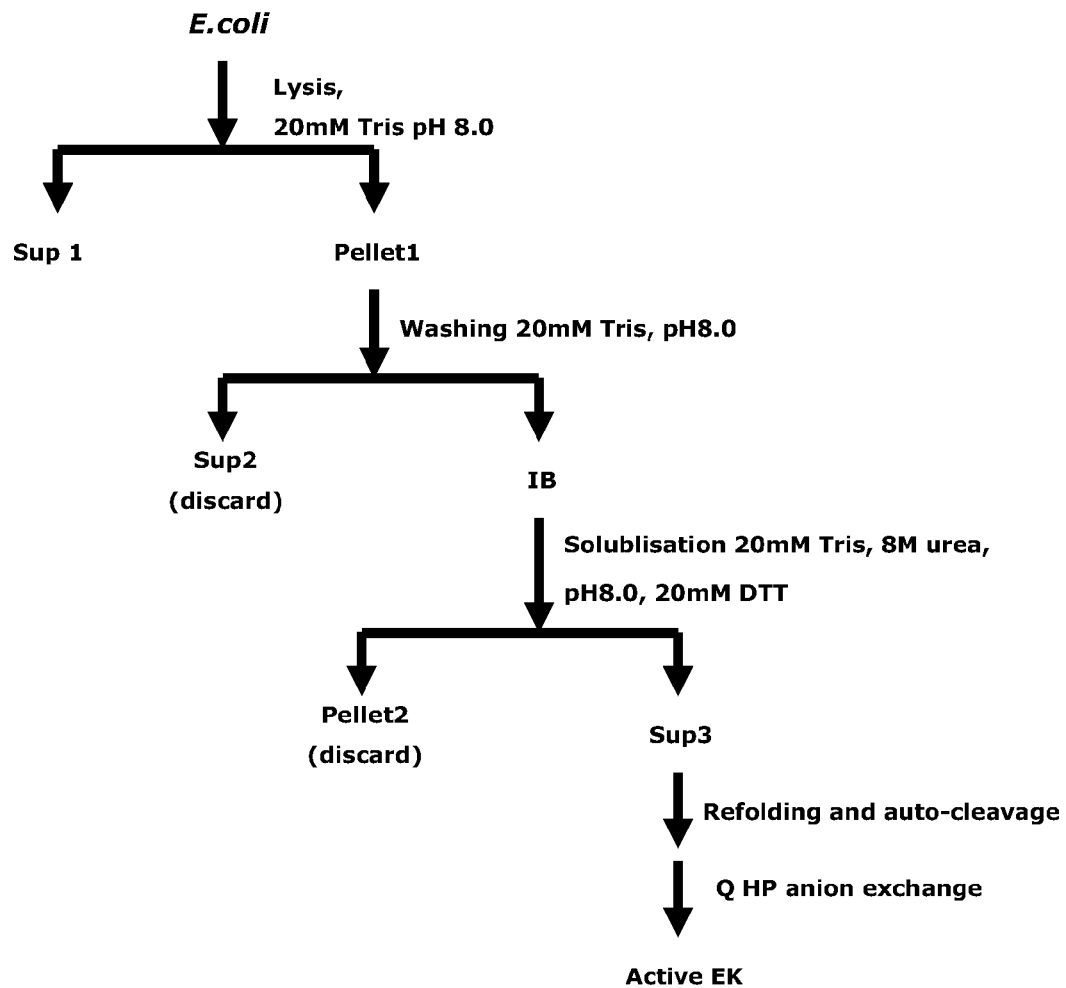
FIG. 2: Flowchart for EK purification
Figure 3A:
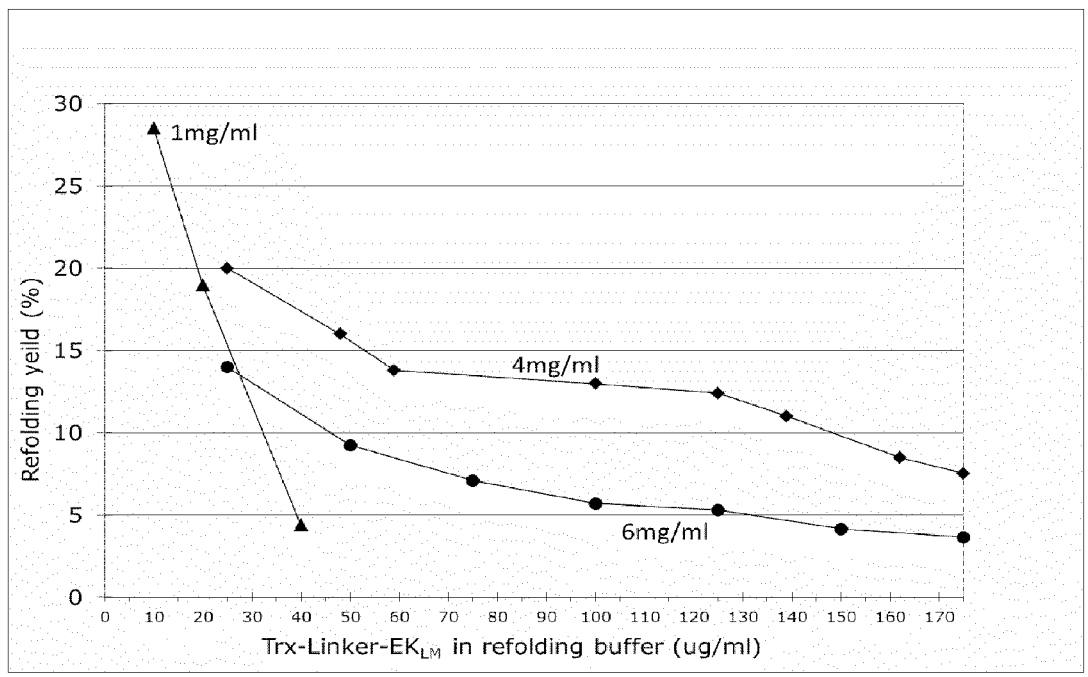
FIG. 3: % refolding yield (FIG. 3A) and the amount of purified $EK_L$ and $EK_{LM}$ in 1 L refolding buffer (mg, FIG. 3B) as a function of the Trx-linker-$EK_L$ and Trx-linker-$EK_{LM}$ concentration during refolding. ▲/△: Trx-linker-$EK_L$, 1 mg/ml inclusion body (IB); ●/○: Trx-linker-$EK_{LM}$, 6 mg/ml IB; ♦/◇: Trx-linker-$EK_{LM}$, 4 mg/ml IB. 1.3 g cell pellets of Trx-linker-$EK_{LM}$ or Trx-linker-$EK_L$ were lysed and inclusion bodies were solublized to different concentrations, i.e. 1 mg/ml for Trx-linker-$EK_L$, 4 mg/ml or 6 mg/ml for Trx-linker-$EK_{LM}$ in buffer containing 20 mM Tris, 8 M urea, pH8.0, 20 mM DTT. After dilution to the concentrations as indicated in the refolding buffer containing 20 mM Tris, 1 M Urea, 1 mM GSSG, 3 mM GSH, pH 8.3 and incubation at 20° C. for 24 hrs, the $EK_{LM}/EK_L$ was subjected to purification by Q HP chromatography as described in Experiments.
Figure 3B:
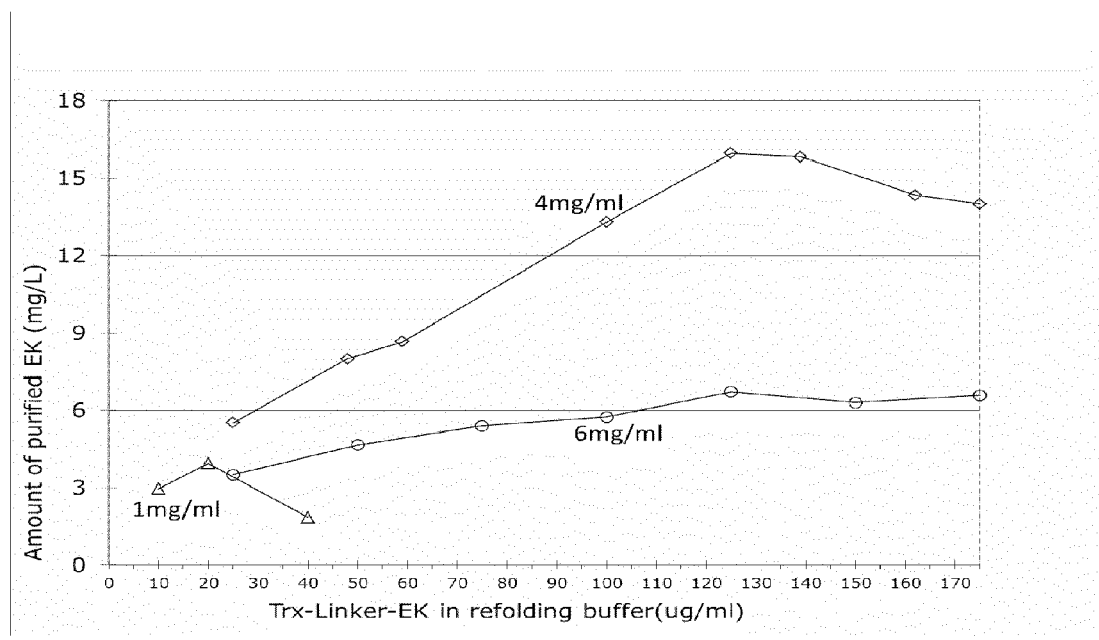

The process scheme is shown in FIG. 2. The inclusion bodies were solublized in the buffer containing 5-8 M urea and 10-20 mM DTT. It should be noted that the inclusion body concentration affected the refolding yield. It was found that the refolding yield of 4 mg/ml Trx-linker-EK$_{LM}$ was 2 fold higher than that of 6 mg/ml Trx-linker-EK$_{LM}$ (FIG. 3A).

The refolding occurred by dilution. The amount of purified enzyme from a fixed volume was also dependant upon the Trx linker EK concentration in the refolding buffer, and reached a maximum when Trx-linker-EK$_{LM}$ concentration was 120 µg/ml.

Figure 4:
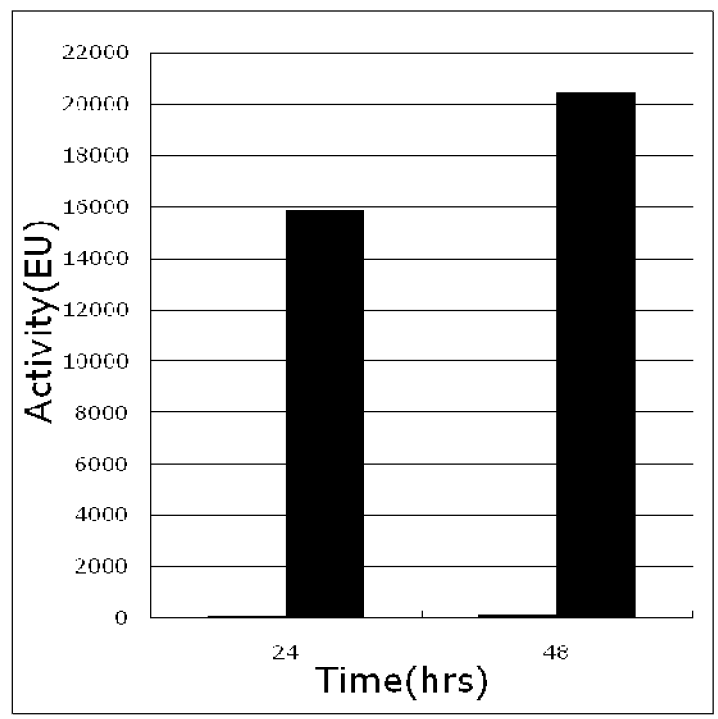
FIG. 4: The refolding yield of Trx-$EK_L$ increases with incubation time. 1.3 g cell pellets of Trx-$EK_L$ were lysed and inclusion bodies were solublized to 1.6 mg/ml in buffer containing 20 mM Tris, 8 M urea, pH8.0, 20 mM DTT. After 100 fold dilution in the refolding buffer containing 20 mM Tris, 1 M Urea, 1 mM GSSG, 3 mM GSH, pH 8.3 and incubated at 20° C. for 24 hrs or 48 hrs, respectively, the enzyme activity was assayed as described in Experiments.
Figure 5:
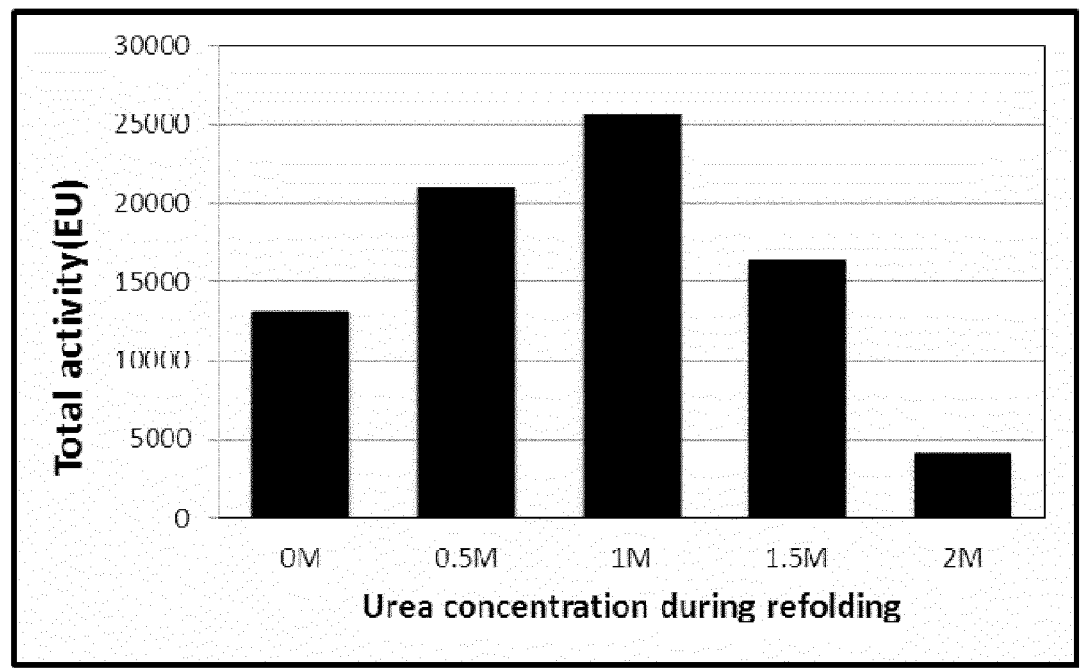
FIG. 5: Dependence of the refolding yield upon urea concentration. 1.3 g cell pellets of Trx-$EK_L$ were lysed and inclusion bodies were solubilized to 1.6 mg/ml in buffer containing 20 mM Tris, 8 M urea, pH8.0, 20 mM DTT. After 100 fold dilution in the refolding buffer containing 20 mM Tris, 1 mM GSSG, 3 mM GSH, pH 8.3 and 0 mM, 0.5 mM, 1 mM, 1.5 mM or 2 mM urea, respectively, and incubated at 20° C. for 24 hrs, the enzyme activity was assayed as described in Experiments.

The auto-catalytic activation occurred concomitantly with the refolding process. The active EK was liberated from Trx-linker-EK by the escape active EK, which specifically cleaved Trx tag off at DDDDK recognition site just before the mature EK. The refolding and auto-catalytic activation process seemed optimal at 48 hrs (FIG. 4). Considering the inhibition of EK by urea, it was found that the refolding yield was largely reduced if above 2 M urea in refolding buffer. Our result showed that 1 M urea in refolding buffer was optimal (FIG. 5).

Figure 6:
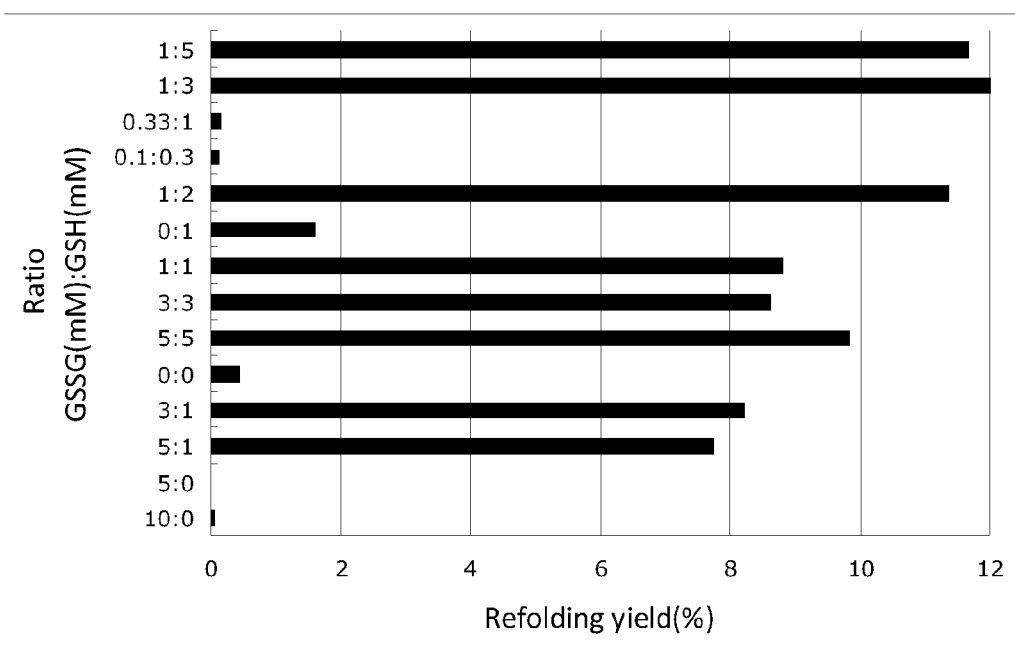
FIG. 6: Dependence of the refolding yield with redox GSSG/GSH ratio. 1.3 g cell pellets of Trx-$EK_L$ were lysed and inclusion bodies were solublized to 1.6 mg/ml in buffer containing 20 mM Tris, 8 M urea, pH8.0, 20 mM DTT. After 100 fold dilution in the refolding buffer containing 20 mM Tris, 1 M Urea, pH 8.3 and GSSG/GSH as indicated, and incubated at 20° C. for 24 hrs, the enzyme activity was assayed as described in Experiments.

The refolding yield was dependent upon the redox system. GSSG/GSH in the ratio 1:3 was found optimal and better than Cystine/cystein (FIG. 6).

Figure 7:
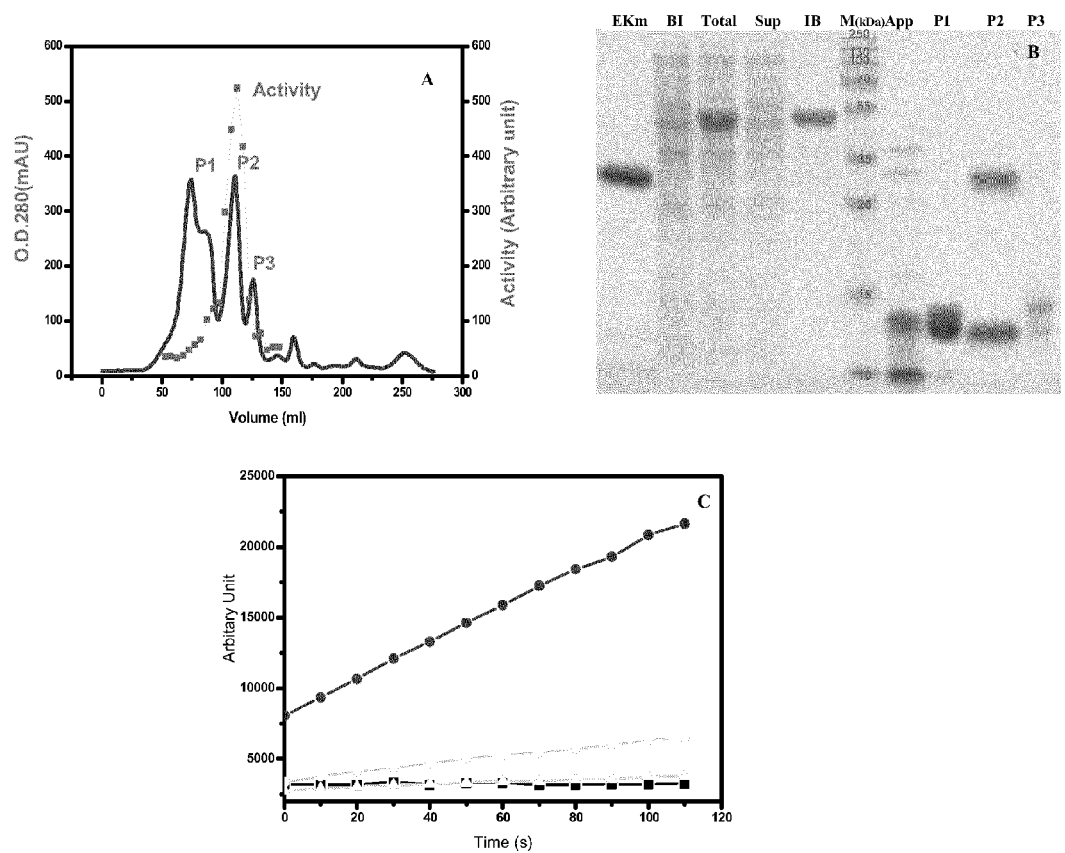
FIG. 7: Purification of $EK_{LM}$ by Q HP chromatography. (A): A chromatogram. $EK_{LM}$ was eluted by sodium gradient, as shown in P2. The fractions containing EK enzymatic activity were indicated. (B): SDS-PAGE of $EK_{LM}$ at each step under reduced conditions. $EK_{LM}$: High purity $EK_{LM}$ (>90%) obtained from further purification of P2 by Hydrophobic Interaction Chromatography; M: Marker, BI: Before Induction, Total: Total lysates; Sup: Supernatant after lysis of cells; IB: Inclusion bodies subjected to refolding and purification; App: Samples applied to Q HP column after refolding and auto-activation; P1, P2 and P3 represent the pooled fractions of each peak indicated in FIG. 7A. (C): Enzymatic activity. △:P1. 1 ul of sample added to 100 ul of reaction buffer; ●: P2. After 5 fold dilution of P2, 1 ul of diluted sample added to 100 ul of reaction buffer; ○: P3. 1 ul of sample added to 100 ul of reaction buffer; ■: Blank. 1 ul of buffer (20 mM Tris, pH 8.0) added to 100 ul of reaction buffer. 1.3 g cell pellets of Trx-$EK_{LM}$ were lysed and inclusion bodies were solubilized to 4 mg/ml in buffer containing 20 mM Tris, 8 M urea, pH8.0, 20 mM DTT. After 80 fold dilution into refolding buffer containing 20 mM Tris, 1 M Urea, 1 mM GSSG, 3 mM GSH, pH 8.3 and incubated at 20° C. for 24 hrs, the $EK_{LM}$ was subjected to purification by Q HP chromatography as described in Experiments.

The active EK after refolding and auto-activation was purified and concentrated by one step anion exchange chromatographic purification (QHP column, FIG. 7A). It was found that Trx tag was in P1, EK$_{LM}$ was mainly in P2 together with the impurity of Trx tag, and P3 contained trace amount of EK$_{LM}$, which is confirmed by the activity assay shown in FIG. 7C. It should be noted that high purity EK$_{LM}$ (>90%) was obtained by further purification of P2 using hydrophobic interaction chromatography (HIC) (FIG. 7B). Moreover, the enzymatic activity of each fraction was also assayed (FIG. 7C), and pooled. For Trx-linker-$EK_L$, the refolding yield was rather low beyond 40 μg/ml of Trx-linker-$EK_L$ during the refolding process (4.4% at 40 μg/ml), which made this process practically difficult. In other words, a huge holding tank is required to produce large amount of EK (~1,000 g).

The low refolding yield could be due to protein aggregation caused by protein hydrophobic interactions. After surface hydrophobicity mapping of $EK_L$ based on its 3D structure, it was found that the $^{133}$ALIY is one of the most hydrophobic patches on the surface. Therefore, $EK_{LM}$ with 3 substitutions (C112A, L134K and I135K) was constructed and subjected to study. By using the exact same process, $EK_{LM}$ greatly improved the refolding yield, especially when $EK_{LM}$ concentration in refolding buffer was beyond 40 μg/ml, which is the bottle neck for the large scale production of $EK_L$ (FIG. 3A). As shown in FIG. 3A, at 40 μg/ml of Trx-linker-$EK_{LM}$ concentration in the refolding buffer, the refolding yield of Trx-linker-$EK_{LM}$ (17%) was 4 fold higher than that of Trx-linker-$EK_L$ (4.4%). Moreover, ~16 mg of active $EK_{LM}$ could be purified from 1 L refolding tank in which the $EK_{LM}$ concentration is 120 μg/ml.

Figure 8:
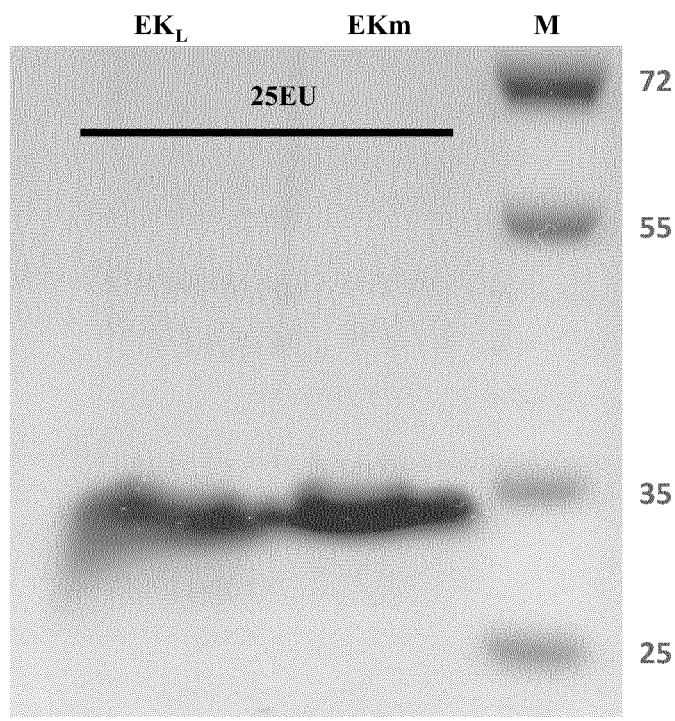
FIG. 8: Similar specific enzymatic activity between $EK_L$ and $EK_{LM}$. 25 EU of purified $EK_L$ and $EK_{LM}$ was loaded on SDS-PAGE.
Figure 9:
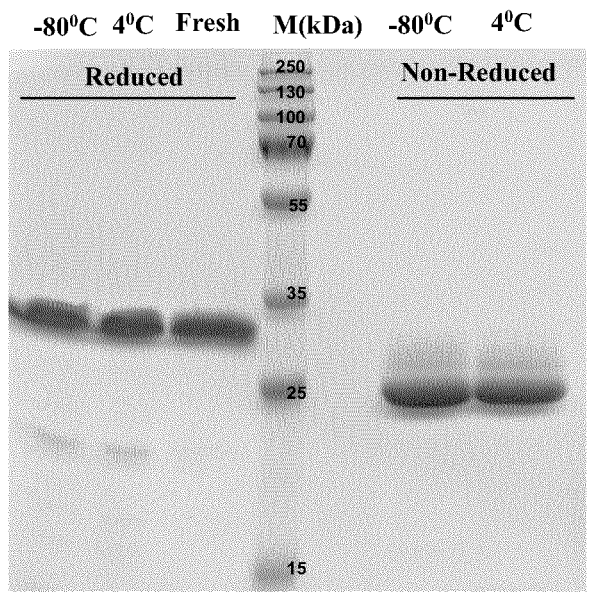
FIG. 9: $EK_{LM}$ is stable for at least 3 month at −80° C. or 4° C. The purified $EK_{LM}$ as described in Experiments was aliquoted and stored at −80° C. or 4° C. After 3 month, 5 µg of $EK_{LM}$ from each temperature was loaded on SDS-PAGE under reduced and non-reduced condition, and compared with freshly purified $EK_{LM}$ (Fresh).

The specific enzymatic activity between $EK_L$ and $EK_{LM}$ was compared as in FIG. 8. The triple substitutions of $EK_{LM}$ had no apparent effect on enzyme activity, which was evidenced by the fact that $EK_L$ and $EK_{LM}$ have similar bands on SDS-PAGE if loaded the same activity. Moreover, $EK_{LM}$ was quite stable if stored in buffer containing 20 mM Tris, 200 mM NaCl at −80° C. or 4° C. No apparent degradation and decrease of activity were observed up to 3 months (FIG. 9).

Example 4

Enzyme Assays

The enzymatic activity was measured directly using a fluorogenic substrate, GDDDDK-Beta-naphthylamide. The reaction was started with addition of 1 ul sample into each well of Fluorescent 96 well plate containing 100 ul of reaction buffer. After mixing for 10 seconds, the fluorescence was measured with Fluostar OPTIMA (excitation at 340 nM and emission at 420 nM). The enzyme activity was defined by arbitrary unit (EU), which derived from slope*60/30,000, where the slope represented linear range.

Example 5

Linker Region

Two $EK_{LM}$ amino acid sequences connected to trx were produced where the linker region differed, $trxEK_{LM}$ and trx-linker-$EK_{LM}$ (see FIG. 10). In trx-linker-$EK_{LM}$ the spacer between trx and $EK_{LM}$ is 37 amino acids longer than in $trxEK_{LM}$.

$TrxEK_{LM}$
Cell Disruption and IBs Solubilization 7.41 g $TrxEK_{LM}$ cell pellet was resuspended in 100 ml of lysis buffer (20 mM Tris, pH 8.0), and the cells were disrupted by using a homogenizer under a pressure of 30,000 psi. After the supernatant was discarded, the IBs weighed 3.53 g. The isolated IBs were resuspended in 70 ml of solublization buffer (20 mM Tris, 8 M urea, pH8.0, 20 mM DTT (freshly added)) and incubated at 4° C. for 4 hrs. The solublized samples were clarified by centrifugation.

Refolding of $TrxEK_{LM}$ 16 ml of IBs solution was diluted into 500 ml refolding buffer (20 mM Tris, 1 mM GSSG, 3 mM GSH, 1 M Urea, pH 8.0) and stirred at 20° C. for 54 hrs. The concentration of protein during refolding is 60 μg/ml.

Purification of $TrxEK_{LM}$
Column: Q HP column
Sample buffer: 20 mM Tris, 1 mM GSSG, 3 mM GSH, 0.62 mM DTT, 1 M Urea, pH 8.0
Buffers: Buffer A: 20 mM Tris, pH 8.0
Buffer B: 20 mM Tris, 0.5 M NaCl, pH 8.0
Procedure: 10 CV 100% A
Application at 10 ml/min
5 CV 100% A
7 CV 0% B-70% B
1 CV 70% B-100% B
1.5 CV 100% B
Column volume: 28 ml
Speed: 10 ml/min The elution fractions with highest enzyme activity were combined resulting in a pool volume of 30 ml and total enzyme activity of 14,100 EU. The protein amount was 2.82 mg.

Trx-Linker-$EK_{LM}$
Cell Disruption and IBs Solubilization 66.9 g Trx-linker$EK_{LM}$ cell pellet was resuspended in 1000 ml of lysis buffer (20 mM Tris, pH 8.0), and the cells were disrupted by using a homogenizer under a pressure of 30,000 psi. After the supernatant was discarded, the IBs weighed 22 g and were washed by 1000 ml of 20 mM Tris, pH 8.0 once. After wash, the IBs solution was divided into 6 bottles for centrifugation. After the supernatant was discarded, 41 ml of solublization buffer (20 mM Tris, 8 M urea, pH8.0, 20 mM DTT (freshly added)) was added into one bottle and incubated at 4° C. for 3 hrs. The solublized IBs were clarified by centrifugation and the final volume was 43 ml.

Refolding of Trx-linker-$EK_{LM}$ 9 ml of IBs solution was diluted into 500 ml of refolding buffer (20 mM Tris, 1 M Urea, 1 mM GSSG, 3 mM GSH, pH 8.0) and stirred at 20° C. for 18 hrs. The concentration of protein during refolding was 60 μg/ml.

Purification of Trx-Linker-$EK_{LM}$
Column: Q HP column
Sample buffer: 20 mM Tris, 1 M Urea, 1 mM GSSG, 3 mM GSH, 0.296 mM DTT, pH 8.0
Buffers: Buffer A1: 20 mM Tris, 1 M Urea, pH 8.0
Buffer A2: 20 mM Tris, pH 8.0
Buffer B: 20 mM Tris, 0.5 M NaCl, pH 8.0
Procedure: 10 CV 100% A1
Application at 10 ml/min
5 CV 100% A1
5 CV 100% A2
7 CV 0% B-70% B (100% A2-30% A2)
1 CV 70% B-100% B (30% A2-0% A2)
1.5 CV 100% B
Column volume: 28 ml
Speed: 10 ml/min The enzyme activity of elution fractions 18-23 is higher than the other fractions through activity test. The elution fractions with highest enzyme activity were combined resulting in a pool volume of 30 ml and total enzyme activity of 24,900 EU. The protein amount was 4.98 mg.

Result:

2.82 mg of $EK_{LM}$ protein was produced from 0.5 L of refolding solution when using $TrxEK_{LM}$ when the protein concentration was 60 μg/ml during refolding, whereas 4.98 mg of EK protein was produced from Trx-linker-$EK_{LM}$ version under the same conditions. Thus, the fusion protein with longer linker showed 76% higher of refolding efficiency than the fusion protein with shorter linker.

Example 6

Components Optimization of the Refolding Buffer

Several different additives, including detergents, cyclodextrins, amino acids, PEG (polyethylene glycol) and sugars, were combined into the current refolding buffer (20 mM Tris, 1 M Urea, 1 mM GSSG, 3 mM GSH, pH 8.3) individually to test their capacity to improve the refolding efficiency of Trx-linker-$EK_{LM}$. The refolding process was performed as described in Example 3 with small modifications. Briefly, the inclusion bodies were solubilized to 7.3 mg/ml in the buffer containing 20 mM Tris, 8 M urea, pH8.0, 20 mM DTT, and then the solubilized Trx-linker-$EK_{LM}$ was added into the optimized refolding buffer containing certain additive by 20-fold dilution. The mixture was incubated at 4° C. for 20 hrs and the amount of correctly refolded Trx-linker-$EK_{LM}$ was quantified by protease activity assay as described in Example 4.

Figure 11:
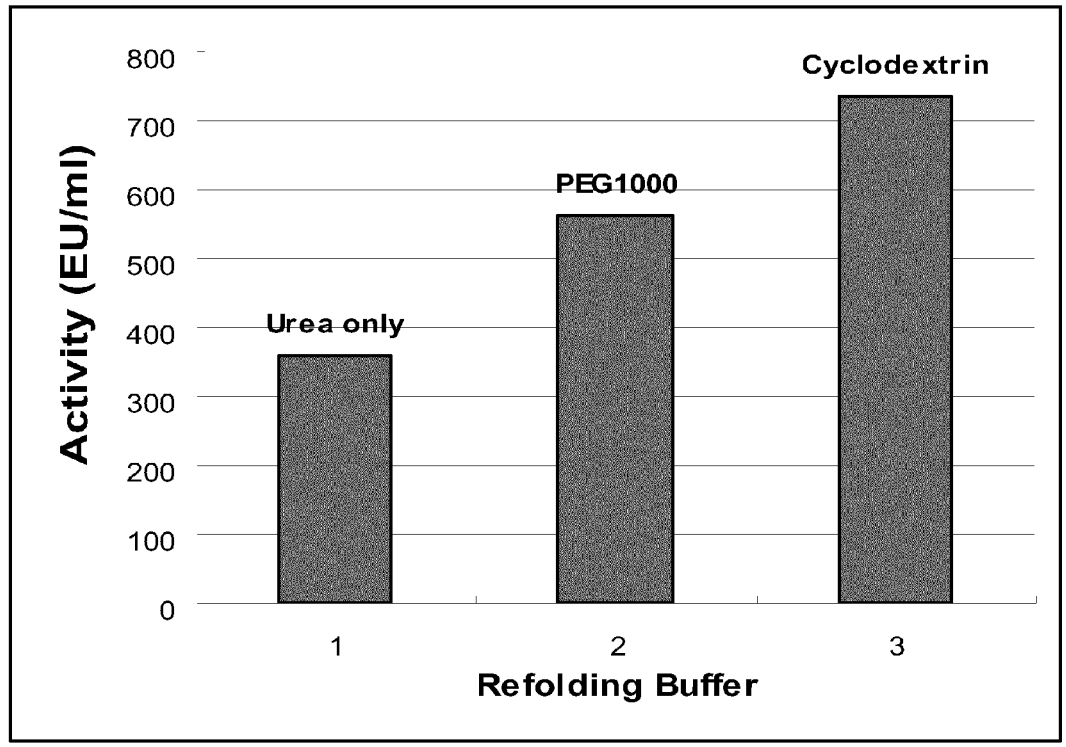
FIG. 11: The refolding efficiency of Trx-linker-$EK_{LM}$ increases with PEG1000 or cyclodextrin added into the refolding buffer. The inclusion body was solubilized into 7.3 mg/ml and diluted with the ratio of 1 to 20 into the refolding buffer. The final concentration of PEG1000 and cyclodextrin in the refolding buffer is 1% and 1.5% respectively.

Both low-PEG (eg.PEG1000, 1%) and hydroxypropyl-β-cyclodextrin (1.5%) exhibited strong capacity to enhance the refolding efficiency of Trx-linker-$EK_{LM}$, with 57.9% and 106.2% increase, respectively, to that from urea-only refolding buffer (as shown in FIG. 11). These two additives have no obvious impact on the maturation of $EK_{LM}$ and the following purification process.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A bovine enterokinase light chain analogue comprising at least one substitution in position 134 and/or 135 from hydrophobic to a hydrophilic charged amino acid(s), wherein the bovine enterokinase light chain analogue is SEQ ID NO:1.

2. The bovine enterokinase light chain analogue according to claim 1, further comprising a substitution in position 112.

3. The bovine enterokinase light chain analogue according to claim 1, wherein the hydrophilic charged amino acid(s) are one or more amino acids selected from the group consisting of: lysine, arginine, glutamic acid and aspartic acid.

4. A bovine enterokinase light chain analogue comprising at least one substitution in position 134 and/or 135 from a hydrophobic to a hydrophilic charged amino acid(s) and a substitution in position 112,
wherein the hydrophilic charged amino acid(s) are one or more amino acids selected from the group consisting of: lysine, arginine, glutamic acid and aspartic acid, and
wherein the bovine enterokinase light chain analogue is SEQ ID NO:1.

5. The bovine enterokinase light chain analogue according to claim 4, wherein the substitution in position 112 is an amino acid selected from the group consisting of: alanine, serine and glycine.

* * * * *

SEQUENCE LISTING

```
<160> NUMBER OF SEQ ID NOS: 9

<210> SEQ ID NO 1
<211> LENGTH: 235
<212> TYPE: PRT
<213> ORGANISM: Artificial Sequence
<220> FEATURE:
<223> OTHER INFORMATION: Bovine Enterokinase light chain

<400> SEQUENCE: 1

Ile Val Gly Gly Ser Asp Ser Arg Glu Gly Ala Trp Pro Trp Val Val
1               5                   10                  15

Ala Leu Tyr Phe Asp Asp Gln Gln Val Cys Gly Ala Ser Leu Val Ser
            20                  25                  30

Arg Asp Trp Leu Val Ser Ala Ala His Cys Val Tyr Gly Arg Asn Met
        35                  40                  45

Glu Pro Ser Lys Trp Lys Ala Val Leu Gly Leu His Met Ala Ser Asn
    50                  55                  60

Leu Thr Ser Pro Gln Ile Glu Thr Arg Leu Ile Asp Gln Ile Val Ile
65                  70                  75                  80

Asn Pro His Tyr Asn Lys Arg Arg Lys Asn Asn Asp Ile Ala Met Met
                85                  90                  95

His Leu Glu Met Lys Val Asn Tyr Thr Asp Tyr Ile Gln Pro Ile Cys
            100                 105                 110

Leu Pro Glu Glu Asn Gln Val Phe Pro Pro Gly Arg Ile Cys Ser Ile
        115                 120                 125

Ala Gly Trp Gly Ala Leu Ile Tyr Gln Gly Ser Thr Ala Asp Val Leu
    130                 135                 140

Gln Glu Ala Asp Val Pro Leu Leu Ser Asn Glu Lys Cys Gln Gln Gln
145                 150                 155                 160

Met Pro Glu Tyr Asn Ile Thr Glu Asn Met Val Cys Ala Gly Tyr Glu
                165                 170                 175

Ala Gly Gly Val Asp Ser Cys Gln Gly Asp Ser Gly Gly Pro Leu Met
            180                 185                 190

Cys Gln Glu Asn Asn Arg Trp Leu Leu Ala Gly Val Thr Ser Phe Gly
        195                 200                 205

Tyr Gln Cys Ala Leu Pro Asn Arg Pro Gly Val Tyr Ala Arg Val Pro
```

```
              210                 215                 220
Arg Phe Thr Glu Trp Ile Gln Ser Phe Leu His
225                 230                 235
```

<210> SEQ ID NO 2
<211> LENGTH: 42
<212> TYPE: DNA
<213> ORGANISM: Artificial Sequence
<220> FEATURE:
<223> OTHER INFORMATION: Primer

<400> SEQUENCE: 2
ggcggtaccg acgacgacga caagattgtc ggaggaagtg ac                                 42

<210> SEQ ID NO 3
<211> LENGTH: 44
<212> TYPE: DNA
<213> ORGANISM: Artificial Sequence
<220> FEATURE:
<223> OTHER INFORMATION: Primer

<400> SEQUENCE: 3
ggcgaattcc taatgtagaa aactttgtat ccactctgtg aacc                               44

<210> SEQ ID NO 4
<211> LENGTH: 45
<212> TYPE: DNA
<213> ORGANISM: Artificial Sequence
<220> FEATURE:
<223> OTHER INFORMATION: Primer

<400> SEQUENCE: 4
acacagatta tatacagcct attgcgttac cagaagaaaa tcaag                              45

<210> SEQ ID NO 5
<211> LENGTH: 45
<212> TYPE: DNA
<213> ORGANISM: Artificial Sequence
<220> FEATURE:
<223> OTHER INFORMATION: Primer

<400> SEQUENCE: 5
cttgattttc ttctggtaac gcaataggct gtatataatc tgtgt                              45

<210> SEQ ID NO 6
<211> LENGTH: 48
<212> TYPE: DNA
<213> ORGANISM: Artificial Sequence
<220> FEATURE:
<223> OTHER INFORMATION: Primer

<400> SEQUENCE: 6
ctattgctgg ctgggggca aagaaatatc aaggttctac tgcagacg                            48

<210> SEQ ID NO 7
<211> LENGTH: 47
<212> TYPE: DNA
<213> ORGANISM: Artificial Sequence
<220> FEATURE:
<223> OTHER INFORMATION: Primer

<400> SEQUENCE: 7
cgtctgcagt agaaccttga tatttctttc cccccagcca gcaatag                            47

<210> SEQ ID NO 8

<211> LENGTH: 393
<212> TYPE: PRT
<213> ORGANISM: Artificial Sequence
<220> FEATURE:
<223> OTHER INFORMATION: trx-linker-EKLM

<400> SEQUENCE: 8

```
Met Ser Asp Lys Ile Ile His Leu Thr Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
                35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
            115                 120                 125

Arg Gly Ser Gly Met Lys Glu Thr Ala Ala Ala Lys Phe Glu Arg Gln
130                 135                 140

His Met Asp Ser Pro Asp Leu Gly Thr Asp Asp Asp Lys Ile Val
145                 150                 155                 160

Gly Gly Ser Asp Ser Arg Glu Gly Ala Trp Pro Trp Val Val Ala Leu
                165                 170                 175

Tyr Phe Asp Asp Gln Gln Val Cys Gly Ala Ser Leu Val Ser Arg Asp
            180                 185                 190

Trp Leu Val Ser Ala Ala His Cys Val Tyr Gly Arg Asn Met Glu Pro
            195                 200                 205

Ser Lys Trp Lys Ala Val Leu Gly Leu His Met Ala Ser Asn Leu Thr
        210                 215                 220

Ser Pro Gln Ile Glu Thr Arg Leu Ile Asp Gln Ile Val Ile Asn Pro
225                 230                 235                 240

His Tyr Asn Lys Arg Lys Asn Asn Asp Ile Ala Met Met His Leu
                245                 250                 255

Glu Met Lys Val Asn Tyr Thr Asp Tyr Ile Gln Pro Ile Ala Leu Pro
            260                 265                 270

Glu Glu Asn Gln Val Phe Pro Pro Gly Arg Ile Cys Ser Ile Ala Gly
        275                 280                 285

Trp Gly Ala Lys Lys Tyr Gln Gly Ser Thr Ala Asp Val Leu Gln Glu
    290                 295                 300

Ala Asp Val Pro Leu Leu Ser Asn Glu Lys Cys Gln Gln Met Pro
305                 310                 315                 320

Glu Tyr Asn Ile Thr Glu Asn Met Val Cys Ala Gly Tyr Glu Ala Gly
                325                 330                 335

Gly Val Asp Ser Cys Gln Gly Asp Ser Gly Gly Pro Leu Met Cys Gln
            340                 345                 350

Glu Asn Asn Arg Trp Leu Leu Ala Gly Val Thr Ser Phe Gly Tyr Gln
            355                 360                 365

Cys Ala Leu Pro Asn Arg Pro Gly Val Tyr Ala Arg Val Pro Arg Phe
        370                 375                 380
```

```
Thr Glu Trp Ile Gln Ser Phe Leu His
385                 390
```

<210> SEQ ID NO 9
<211> LENGTH: 356
<212> TYPE: PRT
<213> ORGANISM: Artificial Sequence
<220> FEATURE:
<223> OTHER INFORMATION: Trx-EKLM

<400> SEQUENCE: 9

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly Gly Thr Asp Asp Asp Asp Lys Ile Val Gly Gly Ser Asp Ser
        115                 120                 125

Arg Glu Gly Ala Trp Pro Trp Val Val Ala Leu Tyr Phe Asp Asp Gln
    130                 135                 140

Gln Val Cys Gly Ala Ser Leu Val Ser Arg Asp Trp Leu Val Ser Ala
145                 150                 155                 160

Ala His Cys Val Tyr Gly Arg Asn Met Glu Pro Ser Lys Trp Lys Ala
                165                 170                 175

Val Leu Gly Leu His Met Ala Ser Asn Leu Thr Ser Pro Gln Ile Glu
            180                 185                 190

Thr Arg Leu Ile Asp Gln Ile Val Ile Asn Pro His Tyr Asn Lys Arg
        195                 200                 205

Arg Lys Asn Asn Asp Ile Ala Met Met His Leu Glu Met Lys Val Asn
    210                 215                 220

Tyr Thr Asp Tyr Ile Gln Pro Ile Ala Leu Pro Glu Glu Asn Gln Val
225                 230                 235                 240

Phe Pro Pro Gly Arg Ile Cys Ser Ile Ala Gly Trp Gly Ala Lys Lys
                245                 250                 255

Tyr Gln Gly Ser Thr Ala Asp Val Leu Gln Glu Ala Asp Val Pro Leu
            260                 265                 270

Leu Ser Asn Glu Lys Cys Gln Gln Gln Met Pro Glu Tyr Asn Ile Thr
        275                 280                 285

Glu Asn Met Val Cys Ala Gly Tyr Glu Ala Gly Gly Val Asp Ser Cys
    290                 295                 300

Gln Gly Asp Ser Gly Gly Pro Leu Met Cys Gln Glu Asn Asn Arg Trp
305                 310                 315                 320

Leu Leu Ala Gly Val Thr Ser Phe Gly Tyr Gln Cys Ala Leu Pro Asn
                325                 330                 335
```

```
Arg Pro Gly Val Tyr Ala Arg Val Pro Arg Phe Thr Glu Trp Ile Gln
            340                 345                 350
Ser Phe Leu His
        355
```